US008877813B2

(12) United States Patent
Kawamura et al.

(10) Patent No.: US 8,877,813 B2
(45) Date of Patent: Nov. 4, 2014

(54) ANTIINFLAMMATORY AND ANALGESIC PREPARATION FOR EXTERNAL USE

(75) Inventors: Youichi Kawamura, Tosu (JP); Yusuke Honda, Tosu (JP)

(73) Assignee: Hisamitsu Pharmaceuticals Co., Inc., Tosu-shi Saga (JP)

( * ) Notice: Subject to any disclaimer, the term of this patent is extended or adjusted under 35 U.S.C. 154(b) by 1065 days.

(21) Appl. No.: 12/898,825

(22) Filed: Oct. 6, 2010

(65) Prior Publication Data

US 2011/0028555 A1 Feb. 3, 2011

Related U.S. Application Data

(62) Division of application No. 11/629,367, filed as application No. PCT/JP2005/010932 on Jun. 15, 2005, now Pat. No. 7,928,144.

(30) Foreign Application Priority Data

Jun. 15, 2004 (JP) ................................ 2004-176722

(51) Int. Cl.

| | |
|---|---|
| ***A61K 31/19*** | (2006.01) |
| ***A61K 8/02*** | (2006.01) |
| ***A61K 9/00*** | (2006.01) |
| ***A61K 31/192*** | (2006.01) |
| ***A61K 31/196*** | (2006.01) |
| ***A61K 47/08*** | (2006.01) |
| ***A61K 9/70*** | (2006.01) |
| ***A61K 9/06*** | (2006.01) |
| ***A61K 9/107*** | (2006.01) |
| ***A61K 47/14*** | (2006.01) |
| ***A61K 9/12*** | (2006.01) |

(52) U.S. Cl.

CPC ............... *A61K 9/107* (2013.01); *A61K 31/192* (2013.01); *A61K 31/196* (2013.01); *A61K 47/08* (2013.01); *A61K 9/7053* (2013.01); *A61K 9/0014* (2013.01); *A61K 9/06* (2013.01); *A61K 9/7076* (2013.01); *A61K 47/14* (2013.01); *A61K 9/12* (2013.01)

USPC ............................ 514/570; 424/400; 424/401

(58) Field of Classification Search

None

See application file for complete search history.

(56) References Cited

U.S. PATENT DOCUMENTS

| | | | | |
|---|---|---|---|---|
| 5,637,293 | A | 6/1997 | Honda | 424/62 |
| 5,707,847 | A * | 1/1998 | Christgau et al. | 435/197 |
| 5,709,847 | A | 1/1998 | Bissett et al. | 424/59 |
| 5,849,272 | A | 12/1998 | Baba et al. | 424/59 |
| 5,891,846 | A * | 4/1999 | Ishida et al. | 514/20.5 |
| 6,927,206 | B2 * | 8/2005 | Patt | 514/2.4 |
| 2004/0220259 | A1 * | 11/2004 | Yu et al. | 514/460 |

FOREIGN PATENT DOCUMENTS

| | | | |
|---|---|---|---|
| EP | 1234573 | A1 | 8/2002 |
| EP | 1234573 | B1 | 7/2005 |
| EP | 1661583 | A1 | 5/2006 |
| FR | 2804024 | | 7/2001 |
| FR | 2804024 | A1 | 7/2001 |
| JP | 60-155111 | | 8/1985 |
| JP | 5-8169 | | 2/1993 |
| JP | 05-178763 | | 7/1993 |
| JP | 7-126121 | | 5/1995 |
| JP | 09-151108 | | 6/1997 |
| JP | 9-291019 | | 11/1997 |
| JP | 2000-136122 | | 5/2000 |
| JP | WO 01/68061 | | 9/2001 |
| JP | 2003 311904 | * | 11/2003 |
| WO | WO 2005023307 | * | 3/2005 |

OTHER PUBLICATIONS

EPO Supplementary Search Report from EPO Application No. 05751470.5, Oct. 5, 2010, EPO.

* cited by examiner

*Primary Examiner* — Alton Pryor

(74) *Attorney, Agent, or Firm* — Licata & Tyrrell P.C.

(57) ABSTRACT

It is intended to provide an antiinflammatory and analgesic preparation for external use whereby side effects of a nonsteroidal antiinflammatory and analgesic drug on the skin can be regulated, the nonsteroidal antiinflammatory and analgesic drug can be prevented from degeneration with time due to a dibenzoylmethane derivative contained as an UV absorbent therein, the dibenzoylmethane derivative can be prevented from crystallization and sedimentation due to an oily phase component contained therein, and the inherent effects of the nonsteroidal anti-inflammatory and analgesic drug can be fully exerted without showing skin irritation caused by the oily phase component, an emulsifier and a thickener. The above problem can be solved by providing an antiinflammatory and analgesic preparation for external use which comprises a base for external use containing an oily phase component, a nonsteroidal antiinflammatory and analgesic drug and a dibenzoylmethane derivative and in which the total amount of fatty acid esters in the oily phase component is at least thrice as much as the content of the dibenzoylmethane derivative.

10 Claims, No Drawings

ANTIINFLAMMATORY AND ANALGESIC PREPARATION FOR EXTERNAL USE

This patent application is a divisional application of U.S. application Ser. No. 11/629,367, filed Dec. 12, 2006 now U.S. Pat. No. 7,928,144, which is the U.S. National Stage of International Application No. PCT/JP2005/010932 filed Jun. 15, 2005, which claims the benefit of priority from Japanese Application No. 2004-176722 filed Jun. 15, 2004, each of which are herein incorporated by reference in their entirety.

TECHNICAL FIELD

The invention relates to a preparation for external use containing a nonsteroidal antiinflammatory and analgesic drug and, in particular, the preparation for external use blended with a UV absorption agent to inhibit effects of light on the nonsteroidal antiinflammatory and analgesic drug.

BACKGROUND ART

Since nonsteroidal antiinflammatory and analgesic drugs such as ketoprofen have an excellent antiinflammatory and analgesic action, they are contained as an active ingredient in patches such as cataplasms and plasters, and in each type of percutaneous pharmaceutical preparations for external use such as gels, creams, ointments and liniments. However, it has been desired to make a preparation an ultraviolet-shielding type because decomposition of the drugs occurs or the photosensitivity appears very rarely.

As a trial to inhibit effects of light on a nonsteroidal antiinflammatory and analgesic drug, an example to try inhibition of formation of photodecomposition products by preventing photodecomposition of ketoprofen, in which a UV absorption agent consisting of a benzophenone derivative is blended to a preparation for external use containing ketoprofen (ref. patent document 1), and the like, have been reported.

In the meantime, although a dibenzoylmethane derivative is known as a UV absorption agent, compatibility with a base of a preparation for external use to the skin is bad, and therefore, it has been difficult to provide a stable preparation blended with the dibenzoylmethane derivative. In order to solve such a problem, blending a special diester (ref. patent document 2) has been tried. In addition, by using a UV protector together with a metal chelate agent, an art to sufficiently exert the effect of the UV protector without deterioration of blended components (ref. patent document 3) and the like have been proposed.

However, inhibition of the effects of light on a nonsteroidal antiinflammatory and analgesic drug and a further preparation type improvement in stability and in efficacy as to a preparation for external use to the skin blended with the benzoylmethane derivative, the above ester and the like, have been desired.

Patent document 1: JP, B, 5-8169 (JP, A, 60-155111)
Patent document 2: JP, A, 9-291019
Patent document 3: JP, A, 2000-136122

DISCLOSURE OF THE INVENTION

Problems to be Solved by the Invention

Consequently, the object of the invention is to provide an antiinflammatory and analgesic medicine for external use, in which side effects of the antiinflammatory and analgesic preparation for external use containing a nonsteroidal antiinflammatory and analgesic drug on the skin are suppressed, there is no skin irritation caused by an oily phase component, an emulsifier and a viscosifier, and the inherent effects of the nonsteroidal antiinflammatory and analgesic drug can fully be exerted preventing degeneration of the preparation.

Means to Solve the Problems

Generally, as to a drug photosensitivity, during extensive research to solve the above problems, it is considered that there are a case occurring due to a non-immunological mechanism when a drug is exposed to sunlight and a case in which a drug made haptenic by exposure of sunlight gives effects to tissues/cells via an immunological mechanism, and the inventors noticed that a preparation for external use with enhanced safety could be provided by inhibiting these two mechanisms in order to prevent the photosensitivity with certainty.

In addition, the inventors found that by blending, in particular, a dibenzoylmethane derivative as a UVA absorption agent absorbing particularly ultraviolet-A (UVA: wave length 320-400 nm) in a preparation, the both effects due to the above immunological mechanism and non-immunological mechanism could remarkably be inhibited. However, the inventors found that blend of a large amount of an oily phase component was indispensable to inhibit crystallization of the dibenzoylmethane derivative in case of using a given amount of the dibenzoylmethane derivative for such inhibition, and accomplished the invention as a result of further investigation.

Namely, the invention relates to an antiinflammatory and analgesic preparation for external use comprising a base for external use and a nonsteroidal antiinflammatory and analgesic drug, wherein the base for external use contains an oily phase component and a dibenzoylmethane derivative in which the total amount of fatty acid esters in the oily phase component is at least thrice as much as the content of the dibenzoylmethane derivative.

The invention also relates to the antiinflammatory and analgesic preparation for external use, wherein the base for external use is emulsified in oil in water type.

The invention further relates to the antiinflammatory and analgesic preparation for external use, wherein the nonsteroidal antiinflammatory and analgesic drug is selected from a group consisting of ketoprofen, tiaprofenic acid, suprofen, loxoprofen, tolmetin, carprofen, flurbiprofen, benoxaprofen, piroxicam, meloxicam, benzydamine, naproxen, felbinac, diclofenac, ibuprofen, diflunisal, azapropazone, etodolac, valdecoxib, celecoxib, rofecoxib, and pharmaceutically acceptable salts thereof.

The invention also relates to the antiinflammatory and analgesic preparation for external use, wherein the derivative is 4-tert-butyl-4'-methoxydibenzoylmethane.

The invention further relates to the antiinflammatory and analgesic preparation for external use, wherein the content of the dibenzoylmethane derivative is 0.5 to 10 weight % based on the total amount of the preparation.

The invention also relates to the antiinflammatory and analgesic preparation for external use, wherein the oily phase component is one or more selected from a group consisting of crotamiton, propylene carbonate, benzyl alcohol, N-methyl-2-pyrrolidone, as well as diisopropyl sebacate, diethyl sebacate, isopropyl myristate, isopropyl palmitate, cetyl isooctanoate and diisopropyl adipate which are liquid fatty acid esters at an ordinary temperature.

The invention also relates to the antiinflammatory and analgesic preparation for external use, wherein the base for external use contains a nonionic surfactant of HLB value 12-16 as an emulsifier.

The invention also relates to the antiinflammatory and analgesic preparation for external use, wherein the nonionic surfactant is one or more selected from polyoxyethylene sorbitan monooleate, polyoxyethylene sorbitan monostearate, polyoxyethylene sorbitan monopalmitate, polyoxyethylene hydrogenated castor oil 40, polyoxyethylene hydrogenated castor oil 60, polyoxyethylene (20) polyoxypropylene (8) cetyl ether and polyoxyethylene (12) cetostearyl ether.

The invention also relates to the antiinflammatory and analgesic preparation for external use, wherein the base for external use further contains a water-soluble polymer as a viscosifier.

The invention further relates to the antiinflammatory and analgesic preparation for external use, wherein the water-soluble polymer is carboxyvinyl polymer.

Effect of the Invention

By containing a dibenzoylmethane derivative as a UVA absorption agent at a high concentration, an antiinflammatory and analgesic preparation for external use of the invention can remarkably inhibit the photosensitivity attributable to a non-steroidal antiinflammatory and analgesic drug. Namely, the antiinflammatory and analgesic preparation for external use of the invention can remarkably inhibit both of effects due to the immunological mechanism and the non-immunological mechanism of the nonsteroidal antiinflammatory and analgesic drug by exerting a UV absorption effect depending on a blend amount of the dibenzoylmethane derivative.

Further, by blending an oily phase component so that the total amount of fatty acid esters in the oily phase component is at least thrice as much as the content of the dibenzoylmethane derivative, an antiinflammatory and analgesic preparation for external use of the invention can very stably be blended with a dibenzoylmethane derivative of a high concentration in a preparation, which was conventionally difficult for making a stable preparation due to its bad compatibility with other bases.

In addition, by blending a nonionic surfactant of HLB value 12-16 as an emulsifier and further a water-soluble polymer as a viscosifier, an antiinflammatory and analgesic preparation for external use of the invention has an excellent physical property in an emulsified condition without separation between an aqueous phase component and an oily phase component even in case of blending a large amount of the oily phase component.

That is, the antiinflammatory and analgesic preparation for external use of the invention certainly inhibits appearance of the photosensitivity due to the immunological mechanism or the non-immunological mechanism of a nonsteroidal antiinflammatory and analgesic drug and can sufficiently exhibit an antiinflammatory and analgesic effect of the nonsteroidal antiinflammatory and analgesic drug, whereby components blended in the preparation can stably exist without being altered with time and there is no skin irritation caused by an oily phase component, an emulsifier and a viscosifier; thus, the antiinflammatory and analgesic preparation for external use having such effects, which contains the nonsteroidal anti-inflammatory and analgesic drug, has been realized for the first time by the invention.

BEST EMBODIMENT FOR CARRYING OUT THE INVENTION

In the following, favorable embodiments of the invention are illustrated in detail.

The nonsteroidal antiinflammatory and analgesic drug which can be used in the antiinflammatory and analgesic preparation for external use of the invention is not particularly limited as long as it is a known antiinflammatory and analgesic drug in which there is a possibility that the photosensitivity appears, and any one may be a target of the invention. Examples of such nonsteroidal antiinflammatory and analgesic drugs include ketoprofen, tiaprofenic acid, suprofen, loxoprofen, tolmetin, carprofen, flurbiprofen, benoxaprofen, piroxicam, meloxicam, benzydamine, naproxen, felbinac, diclofenac, ibuprofen, diflunisal, azapropazone, etodolac, valdecoxib, celecoxib, rofecoxib, and pharmaceutically acceptable salts thereof; among them ketoprofen, tiaprofenic acid, suprofen, and tolmetin, which have a skeleton similar to benzophenone in the structure, are preferable, and ketoprofen having a benzophenone skeleton is particularly preferable. Such nonsteroidal antiinflammatory and analgesic drugs may be used alone or in a combination of two or more members.

The blend amount of the above nonsteroidal antiinflammatory and analgesic drug in the antiinflammatory and analgesic preparation for external use of the invention is not particularly limited; however, it is preferably 0.1 to 10 weight % based on the total amount of the preparation, more preferably 0.5 to 8 weight %, furthermore preferably 1 to 5 weight %.

Although the dibenzoylmethane derivative used in the antiinflammatory and analgesic preparation for external use of the invention is not particularly limited as long as it is a compound which has absorption in a UVA region, examples include 4-tert-butyl-4'-methoxydibenzoylmethane, 2-(4-diethylamino-2-hydroxybenzoyl)benzoic acid n-hexylester, etc.; among them, a particularly preferable dibenzoylmethane derivative is 4-tert-butyl-4'-methoxydibenzoylmethane. 4-tert-butyl-4'-methoxydibenzoylmethane is an excellent UVA absorption agent which has the maximum absorption in ca. 330-360 nm, and Parsol 1789 (manufactured by Roche Co., Ltd.) and the like can be used as a commercial product.

The blend amount of the dibenzoylmethane derivative in the antiinflammatory and analgesic preparation for external use of the invention is not particularly limited; however, in order to let it exert an inhibitory effect against influences of the immunological mechanism and the non-immunological mechanism due to the nonsteroidal antiinflammatory and analgesic drug, it is preferably 0.5 to 10 weight % based on the total amount of the preparation, more preferably 1 to 8 weight %, furthermore preferably 2 to 6 weight %.

In the invention, as an oily phase component, one or more selected from crotamiton and fatty acid esters which are liquid at an ordinary temperature can be used. The above oily phase component used in the invention is preferably one which is good in solubility for a nonsteroidal antiinflammatory and analgesic drug, an active ingredient. In addition, in a case that the nonsteroidal antiinflammatory and analgesic drug used in the invention has a carboxyl group, the above oily phase component is preferably a compound having no hydroxyl group in order not to form an ester between the above oily phase component and the nonsteroidal anti-inflammatory and analgesic drug.

Although as to crotamiton, propylene carbonate, benzyl alcohol and N-methyl-2-pyrrolidone in the antiinflammatory and analgesic preparation for external use of the invention, any one can be used as an oily phase component excellent in solubility for the drug, among them crotamiton is one kind of N-substituted-O-toluidine derivatives and excellent in solubility for a wide range of drugs from a fat-soluble drug to a hydrophilic drug, and therefore, it is favorably used in preparations such as patches including cataplasms, plasters, etc., ointments, creams, and the like.

The fatty acid ester used in the antiinflammatory and analgesic preparation for external use of the invention is not particularly limited as long as it is a fatty acid ester which is liquid at an ordinary temperature. Examples of fatty acid esters used in the invention include diisopropyl sebacate, diethyl sebacate, isopropyl myristate, isopropyl palmitate, cetyl isooctanoate, diisopropyl adipate and the like. Among them, diisopropyl sebacate, diethyl sebacate and isopropyl myristate are particularly preferable. Further, in the invention, an ordinary temperature means 15-25° C.

In the antiinflammatory and analgesic preparation for external use of the invention, the total blend amount of one or more selected from the fatty acid esters in the oily phase component is preferably at least thrice as much as the blend amount of the dibenzoylmethane derivative from the viewpoint of solubility of the dibenzoylmethane derivative.

The emulsifier used in the antiinflammatory and analgesic preparation for external use of the invention is preferably a nonionic surfactant of HLB value 12-16 from the viewpoint of emulsification stability and skin irritation. Examples of nonionic surfactants used in the invention include polyoxyethylene sorbitan monooleate (HLB 15.0), polyoxyethylene sorbitan monostearate (HLB 14.9), polyoxyethylene sorbitan monopalmitate (HLB 15.6), polyoxyethylene hydrogenated castor oil 40 (HLB 12.5), polyoxyethylene hydrogenated castor oil 60 (HLB 14.0), polyoxyethylene (20)-polyoxypropylene (8) cetyl ether (HLB 12.5) and polyoxyethylene (12) cetostearyl ether (HLB 13.5) and the like. Such nonionic surfactants may be used alone in one member or in a combination of two or more members.

Although the water-soluble polymer used in the antiinflammatory and analgesic preparation for external use of the invention is not particularly limited as long as it is a compound to increase the emulsification stability of a base for external use as a viscosifier, in use together with the nonionic surfactant of HLB value 12-16 it is desirably a synthetic water-soluble polymer from the viewpoint of stabilizing supportingly the emulsification condition of oil in water type. Examples of synthetic water-soluble polymers used in the invention include polyvinylpyrrolidone, carboxyvinyl polymer, acrylic acid and alkyl methacrylate copolymer, methylcellulose, hydroxypropyl cellulose, hydroxypropylmethyl cellulose and polyvinyl alcohol (partially hydrolyzed), and in particular, carboxyvinyl polymer is favorably used. In the point of excellent homogeneity with other blend components, carboxyvinyl polymer of average molecular weight of 1250000-4000000 is preferable, and particular preference is given to carboxyvinyl polymer of average molecular weight of 3000000.

The blend amount of the water-soluble polymer in the antiinflammatory and analgesic preparation for external use of the invention is not particularly limited; however, it is preferably 0.1 to 5 weight % based on the total amount of the preparation, more preferably 0.5 to 3 weight %, furthermore preferably 1 to 2 weight %.

By containing the dibenzoylmethane derivative, the oily phase component, the emulsifier and the viscosifier in the preparation of the invention, the nonsteroidal antiinflammatory and analgesic drug is not degenerated, the emulsification stability is kept, and the inherent effects of the nonsteroidal antiinflammatory and analgesic drug is not inhibited.

Further, as required, the antiinflammatory and analgesic preparation for external use of the invention may appropriately be blended with an additive generally used as a preparation for external use other than the above components. As a component which may be blended, examples include a moisturizer, antiseptic, antioxidant, inorganic type ultraviolet absorption agent, perfume and the like.

As moisturizers, examples include lower alkanetriol of carbon number 3-6 or lower alkanediol of carbon number 2-5 such as glycerin, sorbitol, 1,3-butylene glycol and propylene glycol. Among them, 1,3-butylene glycol and propylene glycol are preferable. The moisturizer may be blended in 1-60%, preferably 10-50% based on the total weight, 100 weight %, of the antiinflammatory and analgesic preparation for external use of the invention.

As antioxidants, examples include ascorbic acid stearate, sodium ascorbate, tocopherol (d-compounds, l-compounds and dl-compounds of $\alpha$-tocopherol, $\beta$-tocopherol, $\gamma$-tocopherol, $\delta$-tocopherol, etc.) and ester derivatives thereof, nordihydroguaiaretic acid, dibutyl hydroxytoluene, butylhydroxyanisol, tert-butylhydroquinone gallate (esters of ethyl, propyl, isoamyl etc.), 1-oxo-3-methyl-4-isopropylbenzene and the like, and other antioxidants. The antioxidant may be blended in 0.01-5%, preferably 0.1-1% based on the total weight, 100 weight %, of the antiinflammatory and analgesic preparation for external use of the invention.

As antiseptics, benzoic acid, sodium benzoate, ethyl p-hydroxybenzoate, propyl p-hydroxybenzoate, butyl p-hydroxybenzoate and the like can be used, and may be blended in 0.01-5%, preferably 0.1-1% based on the total weight, 100 weight %, of the antiinflammatory and analgesic preparation for external use of the invention.

As inorganic type ultraviolet absorption agents, for example, titanium dioxide and zinc oxide are illustrated and can more effectively inhibit effects of light on the nonsteroidal antiinflammatory and analgesic drug by blending together with the dibenzoylmethane derivative. The inorganic type ultraviolet absorption agent may be blended in 0.01-5%, preferably 0.1-2% based on the total weight, 100 weight %, of the antiinflammatory and analgesic preparation for external use of the invention.

As perfumes, for example, l-menthol, mentha oil, eucalyptus oil, limonene, isopulegol and other essential oils are illustrated. The perfume may be blended in 0.01-5%, preferably 0.1-1% based on the total weight, 100 weight %, of the antiinflammatory and analgesic preparation for external use of the invention.

A dosage form of the antiinflammatory and analgesic preparation for external use related to the invention is not particularly limited, and can be prepared into creams, lotions, gels, ointments, sticks, aerosols, plasters, etc. Here, as to each of the preparations for external use, the formulation examples of the invention are shown.

First, a cream is described. A cream base contains any one of the dibenzoylmethane derivatives (for example, 4-tert-butyl-4'-methoxydibenzoylmethane), which are characteristics of the invention and a fatty acid ester, and is additionally selected from each type of bases which are known or usually used. For example, a higher fatty acid ester, lower alcohol, hydrocarbon, polyol, higher alcohol, emulsifier, antiseptic, absorption enhancer and antioxidant are illustrated. By blending a nonsteroidal antiinflammatory and analgesic drug which is an active ingredient and, if necessary, appropriately other additives to each base described above, a cream of the invention can be obtained.

In the following, one of preparation examples of creams is shown.

Preparation Example 1

Ketoprofen 3 g was added with benzyl alcohol 2 g, diisopropyl sebacate 5 g and isopropyl myristate 10 g, heated and dissolved. Then, the obtained solution was added with BM-DBM 5 g, diethyl sebacate 10 g and polyoxyethylene sorbitan monostearate 5 g, heated and dissolved. Further, the solution was added with a water phase in which 1,3-butylene glycol 5 g and methylparaben 0.2 g were dissolved in a purified water 43.2 g at 50° C., and emulsified. This solution was added with carboxyvinyl polymer 0.8 g and stirred till homogeneity to obtain the cream preparation blended with ketoprofen.

Then, a lotion is described. A lotion base contains any one of the dibenzoylmethane derivatives (for example, 4-tert-butyl-4'-methoxydibenzoylmethane), which are characteristics of the invention and a fatty acid ester, and is additionally selected from each type of bases which are known or usually used. By blending a nonsteroidal antiinflammatory and analgesic drug and, if necessary, appropriately other additives to base components, for example, such as an alcohol (monohydric alcohols such ethanol and isopropanol, polyols such as polyethylene glycol, propylene glycol and butylene glycol, etc.), water, a surfactant and the like, a lotion of the invention can be obtained.

Preparation Example 2

Felbinac 1 g was added with crotamiton 2 g, isopropyl myristate 5 g, polyoxyethylene sorbitan monostearate 5 g, macrogol 400 5 g and BM-DBM 0.5 g, heated and dissolved. This was added with a water phase in which 1,3-butylene glycol 5 g was dissolved in a purified water 66.1 g, and stirred to obtain the lotion preparation blended with felbinac.

Then, a gel is described. As to a gel base, any one of the dibenzoylmethane derivatives (for example, 4-tert-butyl-4'-methoxydibenzoylmethane) which are characteristics of the invention, and appropriately a base selected from a group from a polyol which is a known gel base, water, a gelatinizing agent (for example, carboxyvinyl copolymer, hydroxyethyl cellulose, hydroxypropyl cellulose, methyl cellulose, carboxymethyl cellulose, polyvinyl alcohol, etc.), a neutralizing agent (for example, triethanolamine, diisopropanolamine, sodium hydroxide, etc.), a surfactant (for example, sorbitan sesquioleate, sorbitan trioleate, sorbitan monooleate, sorbitan monostearate, sorbitan monolaurate, polyethylene glycol monostearate, polyoxyethylene cetylether, polyoxyethylene laurylether, etc.) and an absorption enhancer (for example, an azacycloalkane derivative) are blended, and a gel of the invention can be obtained by blending a nonsteroidal antiinflammatory and analgesic drug.

Preparation Example 3

Ketoprofen 1 g was added with diisopropyl sebacate 2 g and 1,3-butylene glycol 50 g, heated and dissolved. Further, the solution was added with BM-DBM 0.5 g and diethyl sebacate 5 g, heated and dissolved. This solution was added with a swelled solution in which carboxyvinyl polymer 0.7 g was dissolved in a purified water 30.3 g, and stirred to obtain the gel preparation blended with ketoprofen.

Then, an ointment is described. An ointment base contains any one of the dibenzoylmethane derivatives (for example, 4-tert-butyl-4'-methoxydibenzoylmethane), which are characteristics of the invention, and is additionally selected from each type of bases which are known or usually used. Examples include a higher fatty acid ester, wax, surfactant, higher alcohol, silicon oil, hydrocarbon, water, absorption enhancer, moisturizer and antioxidant. By blending a nonsteroidal antiinflammatory and analgesic drug which is an active ingredient and, if necessary, appropriately other additives to each base described above, an ointment of the invention can be obtained.

Preparation Example 4

Ketoprofen 3 g was added with crotamiton 4 g and diisopropyl sebacate 5 g, heated and dissolved. The obtained solution was added with BM-DBM 5 g, white petrolatum 68 g, polysorbate 80 5 g, diethyl sebacate 5 g and isopropyl myristate 5 g, heated and dissolved to obtain the ointment preparation of ketoprofen.

Then, a stick is described. A stick base contains any one of the dibenzoylmethane derivatives (for example, 4-tert-butyl-4'-methoxydibenzoylmethane), which are characteristics of the invention, and is additionally selected from each type of bases which are known or usually used. Examples include a fatty acid metal salt, alcohol, solid fat and water. By blending a nonsteroidal antiinflammatory and analgesic drug which is an active ingredient and, if necessary, appropriately other additives such as a surfactant, antioxidant, perfume and the like to each base described above, a stick of the invention can be obtained.

Preparation Example 5

Diclofenac sodium 2 g was added with diisopropyl sebacate 5 g, diethyl sebacate 3 g, cetyl isooctanoate 2 g, BM-DBM 2 g, sodium stearate 7 g, polyethylene glycol 400 5 g, propylene glycol 13 g, triethanolamine 1 g and isopropanol 60 g, heated and dissolved. The dissolved mixture solution was filled into a container to obtain the stick preparation of diclofenac sodium.

Then, an aerosol is described. An aerosol of the invention is constituted by an undiluted solution and a propellant. The undiluted solution contains any one of the dibenzoylmethane derivatives (for example, 4-tert-butyl-4'-methoxydibenzoylmethane), which are characteristics of the invention, and a fatty acid ester, is additionally selected from each type of bases which are known or usually used, and contains, for example, water, an alcohol or a nonionic surfactant in addition to the above components. Further, other blend components acceptable for the preparation such as a pH adjusting agent, disinfectant, cooling agent, antioxidant, antiseptic, preservative, perfume and the like according to use may be appropriately contained.

In addition, as a propellant of an aerosol of the invention, a known propellant can be used. Examples include dimethyl ether, liquefied petroleum gas, nitrogen gas, carbon dioxide gas, alternative fluorocarbon gas and the like, which are used as a propellant of a usual aerosol.

Preparation Example 6

Ketoprofen 0.5 g was dissolved in ethanol, added sequentially with polyoxyethylene cetostearyl ether 3 g, isopropyl myristate 1 g, BM-DBM 0.2 g and triethanolamine 0.4 g, and stirred. Then, the obtained solution was added with a purified water 25 g and 1,3-butylene glycol 2 g, and further stirred to give the undiluted solution for the aerosol of the invention.

Then, an aerosol can container made of aluminum is filled with the above undiluted solution for the aerosol 70 ml and a liquefied propane gas (LPG) 30 ml as a propellant to obtain the aerosol preparation for external use related to the invention.

Then, a plaster is described. A plaster base contains any one of the dibenzoylmethane derivatives (for example, 4-tert-butyl-4'-methoxydibenzoylmethane), which are characteristics of the invention and a fatty acid ester, and is additionally selected from each type of bases which are known or usually used. As a component contained in such plaster bases, examples include polymer bases (an acrylic composition which is copolymer of vinyl monomers such as methacrylate ester, acryronitrile, vinyl acetate or vinyl propionate, a silicon resin, a polyisoprene rubber, a natural rubber, an acrylic rubber, a styrene-butadiene-styrene block copolymer, a styrene-isoprene-styrene block copolymer, etc.), oils or higher fatty acids (almond oil, olive oil, camellia oil, persic oil, peanut oil, olein oil, liquid paraffin, polybutene, etc.), tackifiers (rosin, a rosin-modified maleic acid ester, a hydrogenated rosin ester, etc.), fatty acid metal salts (zinc undecylenate, zinc stearate, calcium stearate, aluminum stearate, magnesium stearate, sodium stearate, sodium laurate, zinc laurate, etc.) and rash preventing agents. Other blend components acceptable for the preparation such as a disinfectant, cooling agent, antioxidant, antiseptic, preservative, perfume and the like may appropriately be contained according to use, while by blending a nonsteroidal antiinflammatory and analgesic drug which is an active ingredient into the plaster base mixed with various components selected among these, a plaster of the invention can be obtained.

Preparation Example 7

Ketoprofen 2 g was added with l-menthol 3 g, BM-DBM 5 g, propylene carbonate 2 g, diisopropyl sebacate 5 g, styrene-isoprene-styrene block copolymer 29.5 g, polyisobutylene 10 g, hydrogenated rosin glycerol ester 15 g, liquid paraffin 14.5 g, diisopropyl adipate 2 g, isopropyl myristate 10 g and zinc stearate 2 g, and stirred to obtain a homogeneous melt. Then, the obtained melt was spread over a polyethylene terephtharate film treated with silicon, covered with a polyester non-woven cloth, transferred by compression, cut to a desired size to obtain the plaster preparation of the invention.

EXAMPLE

In the following, the invention is explained in more detail showing the examples and the test examples in case of using preparations containing ketoprofen, which is the nonsteroidal antiinflammatory and analgesic drug as an active ingredient, and 4-tert-butyl-4'-methoxydibenzoylmethane (BM-DBM) as an ultraviolet absorption agent. The invention, however, is not limited to these examples, and various modifications may be possible without departing from the technical idea of the invention. In addition, in the following examples, "%" means "weight %" unless otherwise specified.

Production of Preparations in Examples and Comparative Examples

First, the preparations were produced by the formulations in Table 1 described below. Specifically, as a process for Examples 1-5, ketoprofen was dissolved in crotamiton, diisopropyl sebacate and isopropyl myristate. Then, an obtained solution was added with BM-DBM, diethyl sebacate, polysorbate 80, heated and dissolved. Further, methyl p-oxybenzoate, l-menthol and carboxyvinyl polymer were added. The total amount was made 100% by a purified water dissolving diisopropanolamine, and stirred at 80° C. to give creams. As for Comparative Examples 1-6, they were also produced in a similar way.

TABLE 1

| | Formulations | Examples | | | | | Comparative Examples | | | | | |
|---|---|---|---|---|---|---|---|---|---|---|---|---|
| Ingredients | (weight %) | 1 | 2 | 3 | 4 | 5 | 1 | 2 | 3 | 4 | 5 | 6 |
| Active ingredient | Ketoprofen | 3.0 | 3.0 | 3.0 | 3.0 | 3.0 | 3.0 | 3.0 | 3.0 | 3.0 | 3.0 | 3.0 |
| Surfactant | Polysorbate 60 | — | — | — | — | — | — | 5.0 | 5.0 | — | — | — |
| Surfactant | Polysorbate 80 | 5.0 | 5.0 | 5.0 | 5.0 | 5.0 | 5.0 | — | — | 5.0 | | — |
| Surfactant | Polyoxyethylene (20) hydrogenated castor oil (HCO-20) | — | — | — | — | — | — | — | — | — | 5.0 | — |
| Surfactant | Polyoxyethylene (23) cetyl ether (BC-23) | — | — | — | — | — | — | — | — | — | — | 4.0 |
| Resolvent | Crotamiton | 2.0 | 2.0 | 2.0 | 2.0 | 2.0 | 2.0 | 2.0 | 5.0 | 2.0 | 2.0 | 2.0 |
| Solubilizer | Diisopropyl sebacate (DIS) | 5.0 | 5.0 | 5.0 | 5.0 | 5.0 | 5.0 | 5.0 | 5.0 | — | 5.0 | 5.0 |
| Base | Isopropyl myristate (IPM) | 10.0 | 10.0 | 10.0 | 10.0 | 10.0 | 10.0 | 15.0 | 15.0 | 10.0 | 10.0 | 10.0 |
| Base | Diethyl sebacate (DES) | 15.0 | 15.0 | 15.0 | 10.0 | 5.0 | 15.0 | — | — | 15.0 | 15.0 | 15.0 |
| Stabilizer | BM-DBM | 10.0 | 5.0 | 2.5 | 8.0 | 6.0 | 0.0 | 10.0 | 10.0 | 10.0 | 10.0 | 10.0 |
| Antiseptic | Methyl p-oxybenzoate | 0.2 | 0.2 | 0.2 | 0.2 | 0.2 | 0.2 | 0.2 | 0.2 | 0.2 | 0.2 | 0.2 |
| Perfume | l-Menthol | 0.2 | 0.2 | 0.2 | 0.2 | 0.2 | 0.2 | 0.2 | 0.2 | 0.2 | 0.2 | 0.2 |
| pH adjusting agent | Diisopropanolamine | 1.0 | 1.0 | 1.0 | 1.0 | 1.0 | 1.0 | 1.0 | 1.0 | 1.0 | 1.0 | 1.0 |
| Viscosifier | Carboxyvinyl polymer | 1.0 | 1.0 | 1.0 | 1.0 | 1.0 | 1.0 | 1.0 | 1.0 | 1.0 | 1.0 | 1.0 |
| Base | Purified water | q.s. | q.s. | q.s. | q.s. | q.s. | q.s. | q.s. | q.s. | q.s. | q.s. | q.s. |
| | Total | 100 | 100 | 100 | 100 | 100 | 100 | 100 | 100 | 100 | 100 | 100 |
| | Total amount of fatty acid esters (wt. %) | 30 | 30 | 30 | 25 | 20 | 30 | 20 | 20 | 25 | 30 | 30 |
| | BM-DBM:fatty acid ester, ratio | 1:3 | 1:6 | 1:12 | 1:3.1 | 1:3.3 | — | 1:2 | 1:2 | 1:2.5 | 1:3 | 1:3 |
| | HLB value of surfactant | 15.0 | 15.0 | 15.0 | 15.0 | 15.0 | 15.0 | 14.9 | 14.9 | 15.0 | 10.5 | 18.0 |

Test Example 1

Test for Residual Ketoprofen

Using Examples 1-3 in which the UV absorption agent BM-DBM blended in 10, 5.0 or 2.5% in the preparations and Comparative Example 1 in which the blend amount of BM-DBM was made 0%, a remaining ratio of ketoprofen in the preparations was investigated. First, the preparation of about 0.1 g was placed on a glass plate. After irradiation of the glass plate with a UV ray in a given intensity by a UV fluorescent lamp, ketoprofen in the preparations was quantified by a high performance liquid chromatography (HPLC) method to calculate the remaining ratio.

As the results of the test of remaining ketoprofen shown in Table 2, the preparations containing ketoprofen without blend of BM-DBM were 0% in the remaining ratio after irradiation of UV, while it was confirmed that ketoprofen was stabilized in a dose-dependent fashion according to increase of BM-DBM content in the ketoprofen containing preparations blended with BM-DBM.

Test Example 2

Stability Test for Preparation

The preparations of Examples 1, 4 and 5 were used, in which the fatty acid ester content was same and the total amount of the fatty acid esters was three times or more compared with the blend amount of BM-DBM, that is, BM-DBM/fatty acid ratio was different, whereas any of them was not less than 1:3, while as an comparative example, the preparations (Comparative Examples 2-4) in which the total amount of the fatty acid esters is less than three times than the blend amount of BM-DBM, and the preparations were used, in which the HLB value of the emulsifier was less than 12 (Comparative Example 5) and it was not less than 16 (Comparative Example 6), to carry out the stability test. Each preparation was stored under the temperatures of 5° C., 25° C. or 40° C., and changes were observed. The changes of the preparations after three months are shown in Table 2.

As shown by the results in Table 2, in the preparations (Comparative Examples 2-4) in which the total amount of the fatty acid esters is less than three times than the blend amount of BM-DBM, crystallization were observed when stored at 5° C. and 25° C. In addition, the preparation, in which the HLB value of the emulsifier was less than 12 (Comparative Example 5), became separated due to a poor emulsification; the preparation, in which the HLB value of the emulsifier was not less than 16 (Comparative Example 6) formed a polymer aggregate, and an aqueous phase separation was observed when stored at 40° C. On the contrary, as to the preparations of Examples 1, 4 and 5, crystallization were not observed after stored at 5° C. for three months, and change was not found after stored at 40° C. for three months.

TABLE 2

| | Test example 1 Ketoprofen Remaining ratio (%) | Test example 2 Observation results |
|---|---|---|
| Ex. 1 | 99.0 | 5° C.: No crystal after 3 months, 40° C.: No change after 3 months |
| Ex. 2 | 95.1 | — |
| Ex. 3 | 90.2 | — |
| Ex. 4 | — | 5° C.: No crystal after 3 months, 40° C.: No change after 3 months |
| Ex. 5 | — | 5° C.: No crystal after 3 months, 40° C.: No change after 3 months |
| Comp. Ex. 1 | 0.0 | — |
| Comp. Ex. 2 | — | Room temperature: Crystallization |
| Comp. Ex. 3 | — | 5° C.: Crystallization |
| Comp. Ex. 4 | — | 5° C.: Crystallization after 1 week |
| Comp. Ex. 5 | — | Poor emulsification, separation |
| Comp. Ex. 6 | — | Polymer aggregate, 40° C.: Separation of aqueous phase |

Test Example 3

Primary Skin Irritation Test (48 Hr Closed Patch Test)

Two types of samples, that is, Example 1: the preparation of Example 1, and Comparative Example 7: petrolatum, were arranged; about 20 mg of each sample was placed on Finn Chamber (tape for skin sensitization test, Taisho Pharmaceutical Co. Ltd.) and applied on a back part for 28 healthy male adults. After application for 48 hours, the samples were peeled off, and a judgment was carried out at 1 hour and at 24 hours after peel-off. The judgment method was to classify and score a symptom into no reaction, slight erythema, apparent erythema, or erythema and edema, which was evaluated calculating a skin irritation index (SI) according to the equation 1 below. The judgment standard and score of symptoms are as follows. The results obtained are shown in Table 3.

−: No reaction (score 0)

±: Slight erythema (score 0.5)

+: Apparent erythema (score 1.0)

++: Erythema and edema (score 2.0)

TABLE 3

| | | Judgment at 1 hr after peel-off | | | | | | Judgment at 24 hrs after peel-off | | | | | | |
|---|---|---|---|---|---|---|---|---|---|---|---|---|---|---|
| | | Number of persons | | | | Positive Ratio (%) | | Number of persons | | | | Positive Ratio (%) | | Skin irritation |
| No. | Samples | ++ | + | ± | − | ≥+ | ≥± | ++ | + | ± | − | ≥+ | ≥± | index (SI) |
| Ex. 1 | Active | 0 | 0 | 1 | 27 | 0 | 3.6 | 0 | 0 | 0 | 28 | 0 | 0.0 | 1.8 |
| Comp. Ex. 7 | Petrolatum | 0 | 0 | 2 | 26 | 0 | 7.1 | 0 | 0 | 1 | 27 | 0 | 3.6 | 5.4 |

Equation 1

$$SI = \frac{\text{(Total of scores of stronger reactions in judgement after 1 hr and 24 hrs)}}{\text{Number of subjects}} \times 100$$

As shown by the results in Table 3, it became clear that in the preparation of the invention the skin irritation index was in a lower value compared with that of petrolatum, and therefore, it was judged that there is no skin irritation.

Therefore, it is understood that the antiinflammatory and analgesic preparation for external use of the invention inhibits change of a nonsteroidal antiinflammatory and analgesic drug with time, further can contain the nonsteroidal antiinflammatory and analgesic drug and a dibenzoylmethane derivative together in a solution state by blending a large amount of an oily phase component, has an excellent emulsification stability as well as has no skin irritation caused by the oily phase component, an emulsifier and a viscosifier, and is a safe antiinflammatory and analgesic preparation for external use.

Industrial Applicability

As explained above, according to the invention, application as a drug, which is extremely high in stability and has no skin irritation caused by an oily phase component, an emulsifier and a viscosifier, can be expected in an antiinflammatory and analgesic preparation for external use containing a nonsteroidal antiinflammatory and analgesic drug.

What is claimed is:

1. A method for preventing crystallization of 4-tert-butyl-4'-methoxydibenzoylmethane in a preparation comprising a base for external use and ketoprofen or a pharmaceutically acceptable salt thereof, said method comprising blending an oily phase component comprising diethyl sebacate and 4-tert-butyl-4'-methoxydibenzoylmethane into the base for external use so that a total amount of the diethyl sebacate is at least thrice as much as an amount of the 4-tert-butyl-4'-methoxydibenzoylmethane to prevent crystallization of the 4-tert-butyl-4'-methoxydibenzoylmethane from the preparation.

2. The method according to claim 1, wherein the base for external use is emulsified in oil in water type.

3. The method according to claim 1, wherein the oily phase component further comprises one or more selected from a group consisting of crotamiton, propylene carbonate, benzyl alcohol, N-methyl-2-pyrrolidone, as well as diisopropyl sebacate, isopropyl myristate, isopropyl palmitate, cetyl isooctanoate and diisopropyl adipate which are liquid fatty acid esters at an ordinary temperature.

4. The method according to claim 1, wherein the preparation further comprises a drug selected from a group consisting of tiaprofenic acid, suprofen, loxoprofen, tolmetin, carprofen, flurbiprofen, benoxaprofen, piroxicam, meloxicam, benzydamine, naproxen, felbinac, diclofenac, ibuprofen, diflunisal, azapropazone, etodolac, valdecoxib, celecoxib, rofecoxib, and pharmaceutically acceptable salts thereof.

5. The method according to claim 1, wherein the 4-tert-butyl-4'-methoxydibenzoylmethane and ketoprofen or pharmaceutically acceptable salt thereof are in a solution state.

6. The method according to claim 1, wherein the amount of the 4-tert-butyl-4'-methoxydibenzoylmethane is 0.5 to 10 weight % based on the total amount of the preparation.

7. The method according to claim 1, wherein the base for external use contains a nonionic surfactant of HLB value 12-16 as an emulsifier.

8. The method according to claim 7, wherein the nonionic surfactant is one or more selected from polyoxyethylene sorbitan monooleate, polyoxyethylene sorbitan monostearate, polyoxyethylene sorbitan monopalmitate, polyoxyethylene hydrogenated castor oil 40, polyoxyethylene hydrogenated castor oil 60, polyoxyethylene (20) polyoxypropylene (8) cetyl ether and polyoxyethylene (12) cetostearyl ether.

9. The method according to claim 1, wherein the base for external use further contains a water-soluble polymer as a viscosifier.

10. The method according to claim 9, wherein the water-soluble polymer is carboxyvinyl polymer.

* * * * *